United States Patent [19]

Fujikawa

[11] Patent Number: 4,658,120

[45] Date of Patent: Apr. 14, 1987

[54] SENSOR DEVICE FOR USE WITH COOKING APPLIANCES

[75] Inventor: Kuniyoshi Fujikawa, Sakai, Japan

[73] Assignee: Sharp Kabushiki Kaisha, Osaka, Japan

[21] Appl. No.: 715,293

[22] Filed: Mar. 25, 1985

[30] Foreign Application Priority Data

Mar. 28, 1984 [JP] Japan .................................. 59-61942

[51] Int. Cl.$^4$ ............................................. H05B 6/68
[52] U.S. Cl. ............................ 219/505; 219/10.55 B;
219/10.55 E; 99/325; 324/65 R; 374/149
[58] Field of Search ................. 219/10.55 B, 10.55 R,
219/10.55 E, 505, 511, 515; 374/185, 183, 172,
173, 164, 168, 149; 340/599, 595, 584; 99/325;
324/62, 65 R, DIG. 1

[56] References Cited

U.S. PATENT DOCUMENTS

| | | | |
|---|---|---|---|
| 3,887,864 | 6/1975 | Knudsen | 374/168 |
| 4,057,755 | 11/1977 | Piesche | 374/173 X |
| 4,109,129 | 8/1978 | Satoh et al. | 219/10.55 B |
| 4,143,550 | 3/1979 | Kobayashi | 374/172 |
| 4,148,220 | 4/1979 | Spofford | 374/173 |
| 4,484,050 | 11/1984 | Horinouchi et al. | 219/10.55 B |

FOREIGN PATENT DOCUMENTS 54-136450 10/1979 Japan ........................... 219/10.55 R Primary Examiner—Philip H. Leung
Attorney, Agent, or Firm—Birch, Stewart, Kolasch & Birch

[57] ABSTRACT

A sensor device capable of accurately sensor humidity using a pair of sensing elements in which the sensor device contains a pair of sensor elements and are negligibly variable against variations in the physical volume of humidity in comparison to variations in the temperature of these sensor elements. The sensor device is comprised of a pair of sensor elements connected in series, in which one of these generates an output corresponding to the physical volume of humidity while sensing is still underway, whereas the other preserves the output so that it cannot be affected by variations in the physical volume, of humidity while sensor characteristics employed to sense the physical volume of humidity are variable depending on temperature; a current control circuit capable of supplying a large amount of current to a serial circuit comprised of a pair of heaters when the temperature of the sensor elements decreases and conversely supplying a small amount of current to the same circuit when the temperature of the heaters rises; and a sensor detecting any variation in signal output from one of the sensor elements.

2 Claims, 5 Drawing Figures

PRIOR ART

SENSOR DEVICE FOR USE WITH COOKING APPLIANCES

BACKGROUND OF THE INVENTION

The present invention relates to a sensor device that correctly detects the finished level of food cooked, for example, by a microwave oven.

Prior art

Conventional microwave ovens use absolute humidity sensors to detect the finished level of food cooked by radiating microwaves. FIG. 1 is a simplified electrical circuit diagram incorporating an absolute humidity sensor S, that contains a pair of thermistors S1 and S2 for detecting the humidity of exhaust gas from the cooking chamber containing the food. Thermistor S1 is installed so that it comes into constant contact with the exhaust gas. Thermistor S2 is placed in a dry atmosphere free of exhaust gas. Resistor Ra and variable resistor Rb are connected in parallel to the serial circuit composed of thermistors S1 and S2, respectively. When these thermistors are heated, the moisture in the exhaust gas adheres to thermistor S1, thus lowering the temperature of thermistor S1 by latent heat of water. Humidity in the exhaust gas can be detected by determining the difference in the resistance values between thermistor S1 which contacts the exhaust gas and thermistor S2 which is surrounded by dry air. When the humidity reaches a predetermined value, the microwave-generating magnetron stops operating. Conventional microwave ovens contain a pair of thermistors that form an absolute-humidity sensor positioned in the path of the discharged exhaust gas. The two thermistors so contained are equivalent in temperature to the exhaust gas. Accordingly, these two thermistors should contain identical temperature-dependent characteristics. In other words, the difference in the resistance values between these two thermistors should remain constant throughout the entire range of exhaust gas temperature. The temperature of the exhaust gas does vary widely from normal temperature up to 100° C. In some cases, the sensor is operated in temperatures as high as 200° or 250° C. Therefore, it is quite difficult to develop a pair of ideal thermistors that have exactly the same temperature-dependent characteristics throughout the wide temperature range. Likewise, it is also difficult to develop thermistors which precisely hold resistance values at a constant level independent of temperature. This indicates that conventional methods can hardly provide satisfactory results. For example, when using the conventional circuit shown in FIG. 1, if the temperature-dependent characteristics of thermistors S1 and S2 are different from each other, the following problem may develop. If the exhaust gas temperature varies even though there is no humidity in the exhaust at all, as shown in FIG. 2, the judgment level "1" can be easily exceeded. In this case, the sensor will sense incorrectly that there is humidity in the exhaust gas. This will cause the microwave oven to stop operating at the wrong time.

OBJECT AND SUMMARY OF THE INVENTION

The present invention is a sensor device with sensor elements that have identical temperature-dependency characteristics so that sensing operations can be performed with great accuracy. The present invention provides the means for preserving sensor's surface temperature at a constant level by adequately controlling the current flowing through the sensor elements.

One of the preferred embodiments of the present invention provides a pair of sensor elements connected in series. One of these delivers a sensing signal corresponding to the physical volume of humidity, whereas the other controls this output signal so that it can remain unaffected by any variation in the physical volume of humidity. These sensor elements are capable of varying their sensing function against physcial volume depending to temperature. The preferred embodiment provides a current control circuit, which delivers a large current to the serial circuit (comprised of a pair of heaters) when the temperature of the sensor elements decreases. The circuit conversely feeds a small amount of current when the temperature of these sensor elements rises. In addition, the preferred embodiment also provides means for detecting any variations in the signal coming from either of the sensor elements. It also minimizes any variations in the functions of these sensor elements due to a variance in physical volume in response to the temperature of the sensor elements changing.

DETAILED DESCRIPTION OF THE PREFERRED EMBODIMENTS

Figure 1:
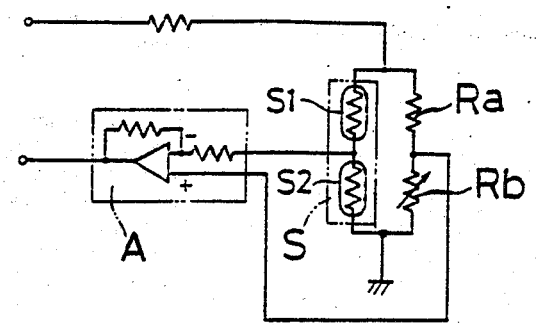
FIG. 1 is a simplified block diagram of an electrical circuit incorporating conventional absolute humidity sensors.
Figure 2:
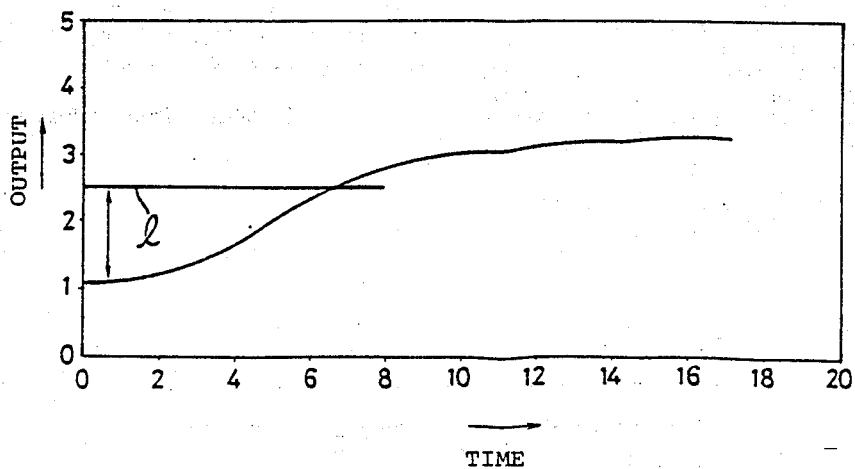
FIG. 2 is a graphic explanation of the relationship between the cooking time and the output of conventional absolute humidity sensors.
Figure 3:
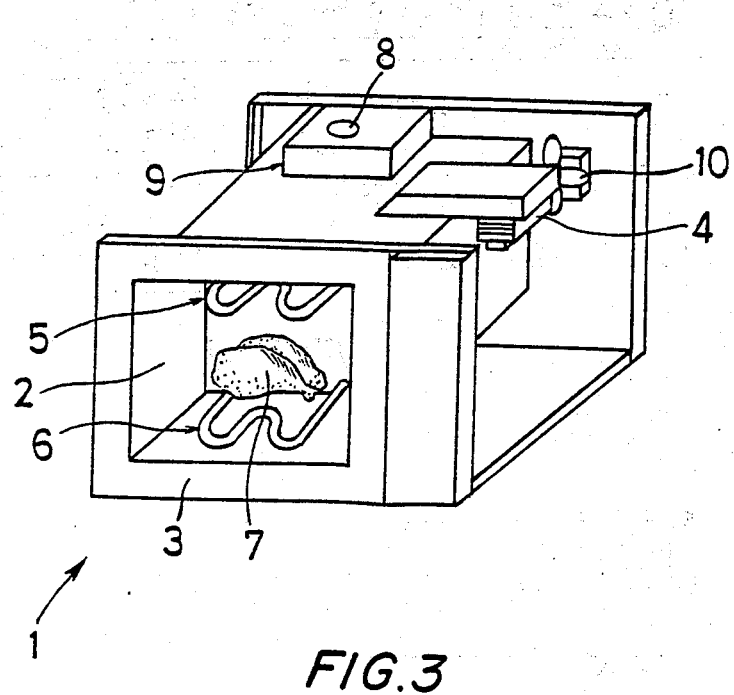
FIG. 3 is a simplified perspective view of a microwave oven incorporating the preferred embodiment of the present invention.
Figure 4:
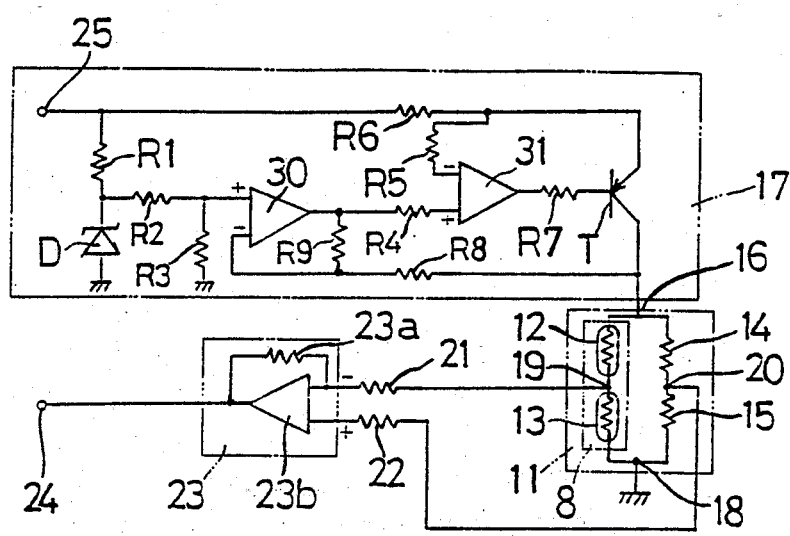
FIG. 4 is the electrical circuit diagram related to the absolute humidity sensor 8 embodied by in the present invention.

FIG. 3 is a simplified perspective view of a microwave oven incorporating the preferred embodiment of the present invention. The cooking chamber (2) is provided with a heating device (4), such as a magnetron, that generates microwaves, as well as two other heating devices (5 and 6). Food is heated by the primary heater (4) and the secondary heaters (5 and 6). The absolute humidity sensor (8) detects the temperature and moisture present in the cooking chamber (2) through the exhaust duct (9), the fan (10) blows air to cool the first heating device (4). FIG. 4 is an electrical circuit related to the absolute humidity sensor (8) embodied by the present invention. The bridge (11) incorporates a pair of thermistors (12 and 13) which serve as the sensor elements. These thermistors (12 and 13) both generate heat by allowing current to flow through them. The first thermistor (12) is an open-type thermistor which contacts directly the exhaust gas coming from the cooking chamber (2). The second thermistor (13) is installed inside a closed dry chamber (not shown) so that its output cannot be affected by any variation in the moisture content. These thermistors (12 and 13) are maintained at a temperature of between 200° and 300° C. by means of the exhaust gas and their own heat generating function. In addition, the bridge (11) also incorporates resistors (14 and 15) which serve as impedance elements. The contact (16) between the thermistor (12) and the resistor (14) is connected to the current control circuit (17). The contact (18) between the thermistor (13) and resistor (15) is grounded. The contact (19) between the thermistors (12 and 13) and the contact (20) between the resistors (14 and 15) are both connected to the input terminal of the operational amplifier (23) via amplifier resistors (21 and 22). The operational amplifier (23) is composed of an amplifier resistor (23a) and an amplifier (23b). The electrical configuration of the current control circuit (17) is described below.

The cathode of Zener diode D is connected to the power supply terminal (25) via the protection resistor (R1), whereas the anode of this Zener diode D is grounded. The junction of the cathod of Zener diode D and protection resistor R1 is connected to the positive terminal of the amplifier (30) via amplifier resistor R2, while this positive terminal is connected to ground via amplifier resistor R3. The output terminal of the amplifier (30) is connected to the positive terminal of the amplifier (31) via protection resistor R4. The negative terminal of the amplifier (31) is connected to the emitter of transistor T via protection resistor R5. The output terminal of the amplifier (31) is connected to the base of the PNP-type transistor T via protection resistor R7. The emitter of transistor T is connected to the power supply terminal (25) via current-detect resistor R6. Collector of transistor T is connected to the contact (16) of the bridge (11). Contact 16 is connected to the negative terminal of the amplifier (30) via amplifier resistor R8. The output terminal of amplifier 30 is connected to the negative terminal of amplifier 30 via amplifier resistor R9.

Next, we summarize the absolute humidity sensor (8). Assume that the thermistors (12 and 13) and the resistors (14 and 15) are provided with identical resistance values. Assume that voltage Vo is delivered to the parallel circuit comprised of the thermistors (12 and 13) and resistors (14 and 15). When no moisture is present, the resistor (15) will receive Vo/2 of the voltage and the thermistor (13) will also receive Vo/2 of the voltage. If the exhaust gas from the cooking chamber (2) contains moisture, the voltage in the resistor (15) remains unchanged. Conversely, the voltage in the thermistor (13) varies. In other words, the temperature on the surface of the thermistor (12) lowers in response to the moisture in the exhaust gas, thus decreasing the resistance value. This causes the voltage of the thermistor (13) to rise. Since the voltage of the thermistor (13) varies due to the effect of the moisture, the presence of moisture can be detected by determining the difference in the voltage between the thermistor (13) and resistor (q5).

Referring now to FIG. 4, the operation of the absolute humidity sensor (8) is described below. When the temperature rises in the cooking chamber, the resistance values of the thermistors (12 and 13) decrease. This causes the difference in the potential at either end of the serial circuit containing the thermistors (12 and 13) to drop to a level lower than when the temperature is normal. The effect of the reduced difference in potentials at both ends of the serial circuit is then transmitted to the negative terminal of amplifier 30 via amplifier resistor R8. Since the signal voltage being fed to the negative terminal of the amplifier (30) itself diminishes, the difference in the potential between the positive and negative terminals of the amplifier (30) increases.

Figure 5:
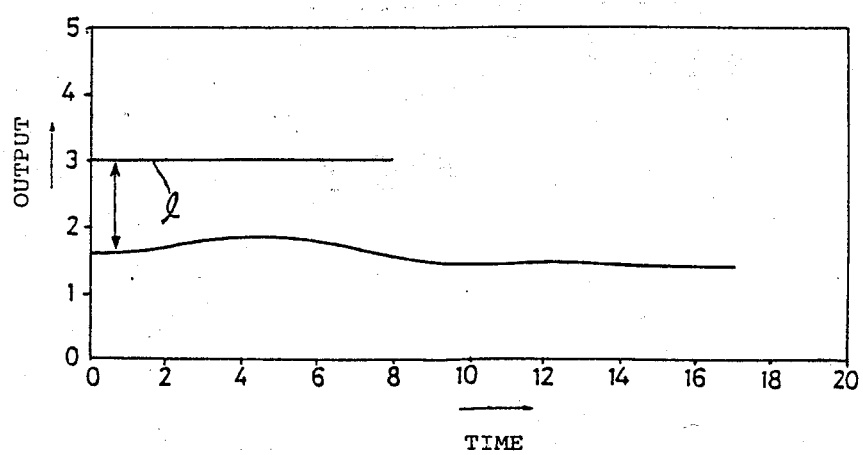
FIG. 5 is a graphic explanation of the rising ambient temperature during cooking and the output of the absolute humidity sensor (8) embodied by the present invention.

As a result, amplifier 30 delivers an output to the positive terminal of amplifier 31 via protection resistor R4 greater than when the temperature is normal. On receipt of such a large signal voltage, the amplifier (31) also outputs a voltage to the base of transistor T via protection resistor R7 greater than when the temperature is normal. On receipt of this, the PNP-type transistor T decreases its amplitude so that current flowing through the bridge (11) is reduced. As a result, the thermistors (12 and 13) reduce the amount of heat they generate. This causes the resitance values in the thermistors (12 and 13) to increase. Since the current flowing through the bridge (11) decreases, any drop in the voltage of the current-detect resistor R6 is extremely reduced, eventually causing the potential of the negative terminal of the amplifier (31) to rise. Actually, the potential of the negative terminal of the amplifier can be stabilized by applying a specific current value predetermined by the amplitude of the current-detect resistor R6, Zener diode D, and amplifier 30. Conversely, when the temperature decreases in the cooking chamber (2), all operations are reversed from those described above. The current flowing through the bridge (11) increases and causes the thermistors (12 and 13) to increase the amount of heat they generate. In other words, any increase or decrease in the current relative to the temperature inside the cooking chamber (2) is dependent on the thermal capacitance of the thermistors (12 and 13). As a result, when the resistance value of the thermistors (12 and 13) decreases as the temperature inside the cooking chamber rises, the amount of current flowing through the thermistors (12 and 13) is decreased. While the cooking proceeds, the temperature of the exhaust gas passing through the exhaust duct (9) varies up to 100° C. from the normal temperature. Immediately after the cooking is completed using the second heating device, the temperature of the exhaust gas normally reaches about 200° C. If the first heating device is then immediately activated, the temperature of the exhaust gas will lower to the normal temperature level. If moisture is still present in the exhaust gas, water adheres to the surface of the thermistor (12). The temperature of the thermistor (12) is lowered by the latent heat generated by vaporization of the water. However, any variation in the temperature of the thermistor (12) effected by latent heat is negligible. Compared to the variations in the temperature of the exhaust gas, which ranges from normal temperature up to 100° C., any variation in temperature due to latent heat is limited to just 1° C. As described above, the current control circuit (17) features a predetermined function relative to the variation in temperature of the thermistors (12 and 13). In the preferred embodiment, this circuit has been designed so that the temperature varies linearly. Based on the reference output value from the output terminal (24) while the exhaust gas is completely dry, any deviation from the reference output value actually corresponds to the amount of moisture remaining in the exhaust gas. The current control circuit (17) prevents any variation in the temperature of the thermistors (12 and 13) caused by the presence of moisture in the exhaust gas. In addition, since the resistance values of the thermistors (12 and 13) can hardly be effected by the presence of moisture in the exhaust gas, even if the variation in the temperature of the thermistors (12 and 3) is neglibible, the slightest variation in the electrical signals caused by the presence of moisture can be delivered to the output terminal (24). FIG. 5 is a graphic explanation of the relationship between the rising temperature of the absolute humidity sensor (8) embodied by the present invention and the output. Even when the heating time of the absolute humidity sensor (8) is extended, if no moisture is present in the exhaust gas, the output value of the output terminal 24 remains constant as shown in FIG. 5. The thermistors, which serve as the sensor elements of the sensor device in conventional devices, usually vary in surface temperature from 0° through 100° C. due to the effect of exhaust gas from the cooking chamber. Thus, it is quite difficult to develop an ideal thermistor having exactly the same temperature characteristics that can accurately respond to a wide range of exhaust gas temperatures. The preferred embodiment of the present invention constricts the variable temperature range of the thermistors to no more than 1° C. As a result, the temperature on the surface of the thermistors remains constant while any variation in the temperature-dependent characteristics of thermistors is practically negligible, thus making it possible to correctly detect the presence of moisture in the exhaust gas.

In the preferred embodiment described above, an explanation has been given based the assumption that the thermistors (12 and 13) had identical resistance values. However, it is possible to correctly detect the presence of moisture in the exhaust gas even if the resistance values of these thermistors are different. In the preferred embodiment described above, a bridge containing resistors was used to correctly identify the reference voltage. However, it is also possible to employ only the thermistors (12 and 13) or to use other compositions so that the variable characteristics of the thermistor (12) affected by humidity can be detected. The conductive elements of the thermistors in the above preferred embodiment concurrently function as heaters in addition to their primary function of generating a specific output corresponding to the physical volume to be detected as humidity.

However, another preferred embodiment may provide sensor elements connected to independent heaters installed in series to control the current flowing into the heater. The preferred embodiment described above employs thermistors as sensor elements. However, these may be substituted by other suitable sensors. Although the foregoing preferred embodiment provides a current control circuit (17) having the configuration described above, this may also be substituted by any other configuration provided that the current can be adequately controlled in response to variations in the actual conditions of the sensor elements.

What is claimed is:

1. A sensor device for detecting the absolute humidity in a chamber, comprising:
   a pair of thermistor elements connected in series and providing a humidity output signal, one of said pair of thermistor elements being responsive to variations in the amount of humidity in the chamber, the other of said pair being unaffected by said variations, the characteristics of said pair of thermistor elements being temperature dependent;
   a pair of impedance elements connected in series with each other and in parallel with said pair of thermistor elements, and providing a reference output signal, said pair of impedance elements and said pair of thermistor elements collectively forming a sensing circuit;
   comparator means having inputs respectively connected to said humidity output signal and said reference output signal for determining the amount of humidity in the chamber; and
   current control means for supplying a relatively large amount of current to the circuit comprised of said thermistor elements and said impedance elements when the temperature of said thermistor elements decreases, and for supplying a relatively small amount of current to said circuit when the temperature of said thermistor elements increases, said current being inversely related to the temperature of said thermistor elements, thereby enabling said comparator means to accurately determine the amount of humidity in the chamber regardless of changes in the temperature of the chamber.

2. The sensor device of claim 1, wherein said current control means comprises:
   detector means for detecting variations in the temperature of said thermistor elements by sensing variations in voltage potential across said thermistor elements;
   control comparator means for comparing said variations in voltage potential with a reference voltage potential and providing an output signal proportional to the difference therebetween; and
   transistor means, responsive to the output signal of said control comparator means, for controlling the amount of current supplied to said circuit.

* * * * *